US 6,589,207 B1
Jul. 8, 2003

(12) United States Patent
El-Nounou

(10) Patent No.: US 6,589,207 B1
(45) Date of Patent: Jul. 8, 2003

(54) RAPID EXCHANGE CATHETER HAVING A SUPPORT MANDREL

(75) Inventor: Fozan El-Nounou, Sunnyvale, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/468,741

(22) Filed: Dec. 21, 1999

(51) Int. Cl.⁷ ............................................. A61M 29/00
(52) U.S. Cl. ................................. 604/103.04; 604/96.01
(58) Field of Search ..................... 604/103.04, 96.01, 604/524, 102.01, 102.02, 102.03, 523, 525

(56) References Cited

U.S. PATENT DOCUMENTS

| | | | |
|---|---|---|---|
| 4,748,982 A | 6/1988 | Horzewski et al. | 128/344 |
| 4,762,129 A | 8/1988 | Bonzel | 128/344 |
| 4,775,371 A | 10/1988 | Mueller, Jr. | 604/280 |
| 5,242,396 A | 9/1993 | Evard | 604/96 |
| 5,389,087 A | 2/1995 | Miraki | 604/247 |
| 5,439,447 A | 8/1995 | Miraki | 604/96 |
| 5,456,680 A | 10/1995 | Taylor et al. | 604/2 |
| 5,458,613 A | 10/1995 | Gharibadeh et al. | 2/95 |
| 5,489,271 A | 2/1996 | Andersen | 604/102 |
| 5,496,346 A | 3/1996 | Horzewski et al. | 606/194 |
| 5,531,690 A | 7/1996 | Solar | 604/102 |
| 5,545,134 A | 8/1996 | Hilaire et al. | 604/96 |
| 5,545,138 A * | 8/1996 | Fugoso et al. | 604/103.1 |
| 5,626,600 A | 5/1997 | Horzewski et al. | 606/194 |
| 5,755,685 A | 5/1998 | Andersen | 604/53 |
| 5,782,740 A | 7/1998 | Schneiderman | 600/1 |
| 5,810,867 A | 9/1998 | Zarbatany et al. | 606/191 |
| 5,823,995 A | 10/1998 | Fitzmaurice et al. | 604/96 |
| 5,868,706 A | 2/1999 | Cox | 604/96 |

FOREIGN PATENT DOCUMENTS

| | | |
|---|---|---|
| EP | 0 829 269 A1 | 3/1998 |
| WO | WO92/17236 | 10/1992 |

* cited by examiner

Primary Examiner—Brian L. Casler
Assistant Examiner—Kevin C. Sirmons
(74) Attorney, Agent, or Firm—Fulwider Patton Lee & Utecht, LLP

(57) ABSTRACT

Rapid exchange catheters having improved pushability and trackability due to a support mandrel disposed within the inflation lumen. The mandrel is secured at the proximal end of the catheter shaft while the free distal end extends beyond the proximal guidewire port. In an alternative embodiment, the catheter shaft further comprises a sleeve in the inflation lumen that secures a distal section of the support mandrel. The distal end of the mandrel extends beyond the sleeve.

15 Claims, 3 Drawing Sheets

RAPID EXCHANGE CATHETER HAVING A SUPPORT MANDREL

BACKGROUND OF THE INVENTION

Catheters designed for intravascular procedures such as angioplasty must have a number of characteristics. Such catheters must be able to transmit force along the length of the catheter shaft to allow it to be pushed through the patient's vasculature. However, the catheter shaft must also retain sufficient flexibility to allow it to track over a guidewire through the often tortuous vasculature. Additionally, the catheter must be able to cross stenosed portions of the vascular anatomy. Prior art designs have supplemented polymer catheter shafts with a stiffening wire or mandrel.

There is a need for rapid exchange catheters having improved pushability, trackability and crossability providing enhanced performance characteristics. The present invention addresses this and other needs.

SUMMARY OF THE INVENTION

The invention is directed to a balloon catheter, preferably a rapid exchange type catheter, having a mandrel in an inflation lumen extending within the catheter shaft. The intravascular balloon catheters of this invention generally comprise an elongated catheter shaft having proximal and distal ends, an inflation lumen extending within the elongated catheter shaft to a location in the distal shaft section of the elongated shaft, and an inflatable balloon disposed on a distal portion of the distal shaft section having an interior in fluid communication with the inflation lumen. A distal port is in the distal end of the catheter shaft, and a proximal port is in the distal shaft section proximal to the inflatable balloon. A guidewire receiving lumen extends through a portion of the catheter shaft, between and in fluid communication with the distal and proximal ports.

A support mandrel is disposed within the inflation lumen and has a proximal end and a free distal end. The proximal end of the mandrel should be secured in a proximal section of the catheter shaft, and the mandrel distal end should extend distally of the proximal guidewire port, and is preferably free.

In one presently preferred embodiment, the guidewire lumen and the inflation lumen are substantially parallel to one another at the proximal guidewire port and become coaxial to one another distal of the proximal guidewire port. The free distal end of the support mandrel should extend in the inflation lumen to at least the area where the guidewire and inflation lumens become coaxial.

In another presently preferred embodiment, the catheter shaft further comprises a sleeve to secure a distal section of the support mandrel to a wall defining the inflation lumen. In this embodiment, the distal end of the mandrel preferably extends beyond the distal end of the sleeve and the sleeve is preferably disposed adjacent to the proximal guidewire port.

The catheter of the invention has improved pushability and crossability while maintaining more than adequate trackability due to the support mandrel in the inflation lumen with a free distal end located distal to the proximal guidewire port. A catheter with the support mandrel of the invention also has excellent resistance to catheter shaft kinking. Further, the design of this invention maximizes the cross sectional area of the inflation lumen along the length of the catheter while accommodating the support mandrel, to consequently improve inflation and deflation times. These and other advantages will become more apparent from the following detailed description and accompanying figures.

DETAILED DESCRIPTION OF THE INVENTION

Figure 1:
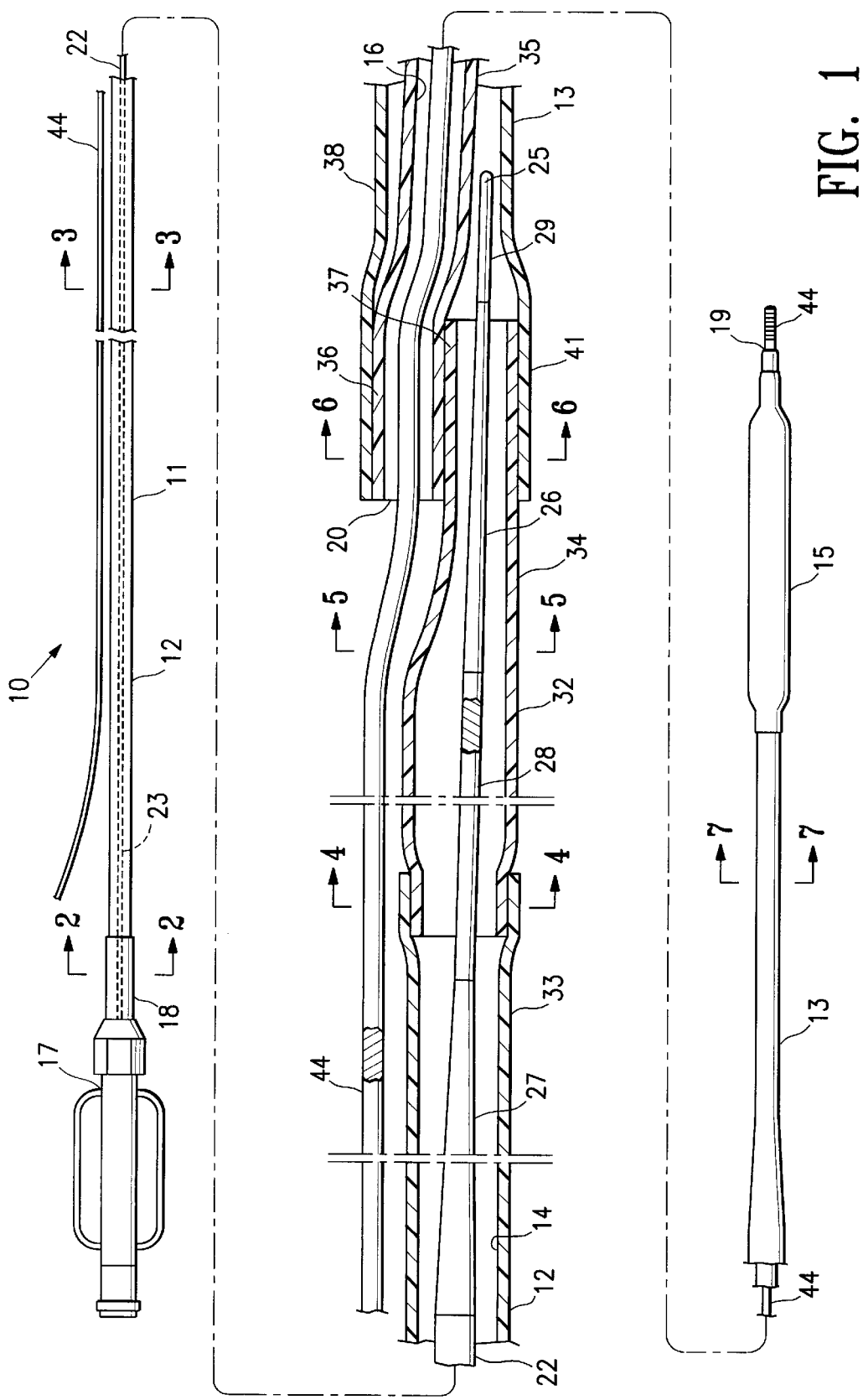
FIG. 1 is an elevational view, partially in section, of a rapid exchange balloon catheter having a support mandrel that embodies features of the invention.

FIGS. 1–7 illustrate a rapid exchange type balloon catheter 10 embodying features of the invention. Catheter 10 generally comprises an elongated catheter shaft 11 having a proximal shaft section 12 and a distal shaft section 13, an inflation lumen 14 adapted to direct inflation fluid from the proximal end of the catheter shaft to the interior of an inflatable balloon 15 on a distal portion of the catheter shaft, and a guidewire lumen 16 extending through distal section 13 of catheter shaft 11. An adapter 17 and strain relief 18 are attached to the proximal end of catheter shaft 11, and adapter 17 is configured to direct inflation fluid into inflation lumen 14. A distal guidewire port 19 at the distal end of catheter shaft 11 and a proximal guidewire port 20 are both in fluid communication with the guidewire lumen 16. Proximal guidewire port 20 in the distal shaft section 13 is proximal to balloon 15 and is spaced a short distance from the distal end of the catheter shaft and a substantially greater distance from the proximal end of the catheter shaft, so that the proximal port is closer to the catheter distal end than to the proximal end. A support mandrel 22 is disposed in inflation lumen 14.

Figure 2:
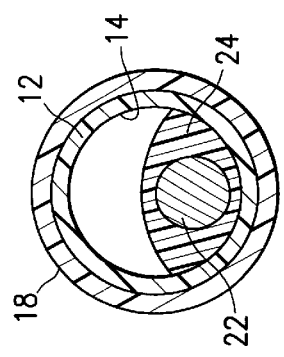
FIG. 2 is a transverse cross-section of the catheter shown in FIG. 1 taken at line 2—2, showing the support mandrel secured in the proximal section of the catheter adjacent the adapter.
Figure 5:
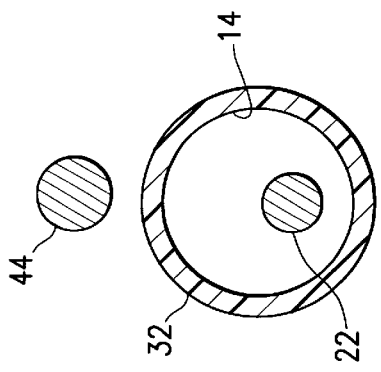
FIG. 5 is a transverse cross-section of the catheter shown in FIG. 1 taken at line 5—5, showing the support mandrel disposed in the intermediate section.

The proximal end 23 of support mandrel 22 is secured at the proximal end of catheter shaft 11, as shown in FIG. 2. Preferably, proximal end 23 of support mandrel 22 is embedded in polymeric material 24, although any conventional method of securing it may be used. The distal end 25 of support mandrel 22 is free, and extends distally beyond proximal guidewire port 20, as illustrated in FIG. 1. In one embodiment, support mandrel 22 is tapered at least at its distal end to provide a smooth transition in flexibility and to maximize the effective cross sectional area of inflation lumen 14. In the embodiment illustrated in FIG. 1, the mandrel has a first tapered section 26 which tapers gradually in a distal direction from a location on the mandrel proximal to the proximal guidewire port 20. In the embodiment illustrated in FIG. 1, the mandrel also has a second tapered section 27 proximal to the first tapered section. The second tapered section 27 preferably is located in a distal portion of the proximal shaft section 12. In FIG. 1, vertical lines are provided on the mandrel to illustrate the location of the tapered sections 26/27, and would not necessarily be visible on the actual mandrel. The first tapered section 26 is typically about 1 to 5 cm long, preferably about 2 to about 3 cm long, and the second tapered section 27 is about 1 to about 12 cm long, preferably about 6 to about 7 cm long. The length of the mandrel from the proximal end of the second tapered section 27 to the distal tip of the mandrel, is typically about 10% to about 30%, preferably about 15% to about 20% of the total length of the mandrel. In the embodiment illustrated in FIG. 1, an intermediate section 28 of the mandrel is provided between the first and second tapered sections 26/27, having a constant diameter. Intermediate section 28 of mandrel 22 is about 5 to about 20 cm long, preferably about 8 to about 10 cm long. Distal end section 29 of mandrel 22 has a constant diameter and is typically about 1 to about 10 cm long, preferably about 1 to about 2 cm long. In one embodiment, the proximal end of the wire may have a diameter of about 0.01 to about 0.02 inch, preferably about 0.019 inch and it may taper to a diameter of about 0.003 to about 0.006 inch, preferably about 0.005 inch at the distal end. Other dimensions may be employed depending upon the construction of the catheter and its desired use. Support mandrel 22 may be formed from a metal wire or other suitable flexible material. Currently preferred materials include stainless steel, MP35N, or nickel-titanium alloys.

In the embodiment of the catheter 10 illustrated in FIG. 1, the catheter shaft has an intermediate section 32 between the proximal shaft section 12 and distal shaft section 13. Preferably, the intermediate section 32 is softer and more flexible than the proximal shaft section, to provide a gradual stiffness transition between the proximal shaft section 12 and the distal shaft section 13, and improve catheter shaft flexibility, maneuverability, and pushability. In one embodiment, the intermediate section 32 is formed of a polymeric material which is softer, i.e., lower Shore Durometer hardness, than the polymeric material forming the proximal shaft section. In the embodiment illustrated in FIG. 1, the first tapered section 26 of mandrel 22 has a proximal end in the intermediate catheter shaft section 32, and a distal end distally beyond the distal end of the intermediate section 32.

Figure 4:
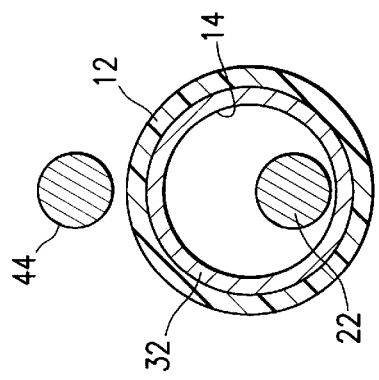
FIG. 4 is a transverse cross-section of the catheter shown in FIG. 1 taken at line 4—4, showing the support mandrel disposed in the inflation lumen at the junction of the proximal section and the intermediate section.
Figure 7:
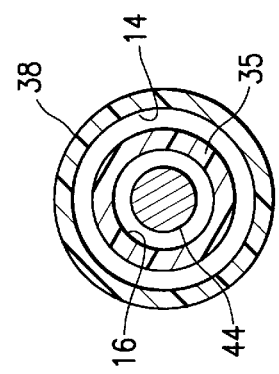
FIG. 7 is a transverse cross-section of the catheter shown in FIG. 1 taken at line 7—7, showing the guidewire disposed in the guidewire lumen of the distal section.
Figure 3:
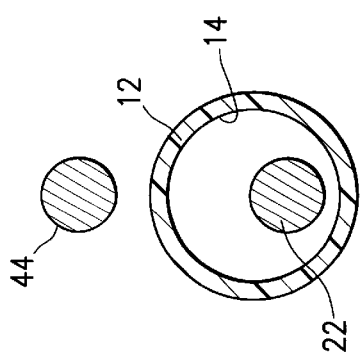
FIG. 3 is a transverse cross-section of the catheter shown in FIG. 1 taken at line 3—3, showing the support mandrel disposed in the inflation lumen of the proximal section.
Figure 6:
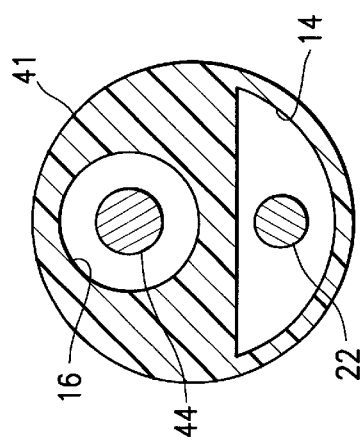
FIG. 6 is a transverse cross-section of the catheter shown in FIG. 1 taken at line 6—6, showing the junction of the intermediate section and the distal section with the support mandrel disposed in the inflation lumen and the guidewire disposed in the guidewire lumen.

The proximal shaft section 12 comprises a proximal tubular member 33 which defines inflation lumen 14 as shown in FIG. 3. Intermediate section 32 comprises an intermediate tubular member 34 which is secured to the distal end of proximal tubular member 33 and which defines a section of the inflation lumen 14 beyond the proximal tubular member 33, as shown in FIG. 4. The distal shaft section 13 comprises an inner tubular member 35 with a proximal section 36 that overlaps a distal section 37 of the intermediate tubular member 34, and an outer tubular member 38 which is disposed around the overlapping sections of the intermediate and distal tubular members to secure the two tubular members together. The outer tubular member 38 distal section is disposed coaxially around the inner tubular member 35. The inner tubular member 35 has a proximal end defining the proximal guidewire port 20 and a distal end defining the distal guidewire port 19. Preferably, the overlapping sections of the intermediate tubular member 34, inner tubular member 35, and outer tubular member 38 are formed from polymeric materials and fused together as illustrated in FIG. 6, wherein inflation lumen 14 may have a generally "D" or semi-circular shape, or a crescent shape following the fusing operation. As shown in FIG. 6, the overlapped and fused sections of the intermediate, inner and outer tubular members form a dual lumen portion 41 of catheter shaft 11 such that inflation lumen 14 and guidewire lumen 16 are substantially parallel in the overlap area. Distal to intermediate tubular member 34, inflation lumen 14 becomes annular and coaxial with guidewire lumen 16, as shown in FIG. 7. In the embodiment illustrated in FIG. 1, the distal end of support mandrel 22 extends beyond proximal guidewire port 20, preferably by a distance of about 1 to about 10 cm, most preferably by about 2.5 cm, and into the coaxial portion of inflation lumen 14. Inflatable balloon 15 is sealingly secured at its proximal end to the distal end of outer tubular member 38 and at its distal end to the distal end of inner tubular member 35.

Figure 8:
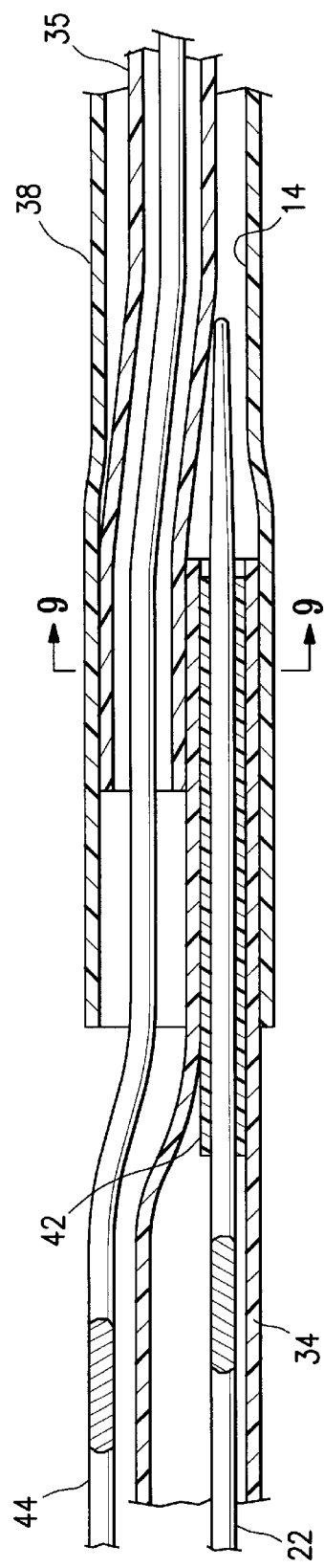
FIG. 8 is a longitudinal cross sectional view of an alternate embodiment of the invention, having a sleeve to secure a distal section of the support mandrel.
Figure 9:
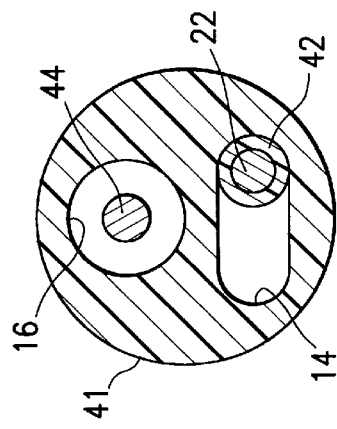
FIG. 9 is a transverse cross-section of the catheter shown in FIG. 8 taken at line 9—9, showing the support mandrel secured in the sleeve.

An alternative embodiment of the invention is shown in FIGS. 8 and 9, wherein catheter 10 further comprises a sleeve 42 around a distal section of the support mandrel 22. Preferably, sleeve 42 is disposed within the inflation lumen and secured to intermediate tubular member 34 to secure a distal section of support mandrel 22. The distal end of support mandrel 28 extends beyond the distal end of sleeve 42 by about 1 to about 10 cm. In the embodiment illustrated in FIG. 9, the sleeve and mandrel therein is offset from the center of the inflation lumen 14 in a side section of the inflation lumen 14. However, in alternative embodiments, the sleeve 42 and mandrel 22 therein may be located in other sections of the inflation lumen 14 (not shown). In the embodiment of FIG. 9, the sleeve is secured to one side of the wall defining the inflation lumen in the intermediate tubular member 34. In one embodiment, sleeve 42 has an outer diameter of about 0.014 in and this provides the inflation lumen 14 adjacent sleeve 42 with dimensions of about 0.007 in by 0.017 in. As shown in FIG. 9, the intermediate, inner, and outer tubular members may be fused to secure them, forming dual lumen portion 41 of catheter shaft 11, as discussed above.

The sections of catheter shaft 11 can be formed by conventional techniques, as for example by extruding, from materials already found useful in intravascular catheters such a polyethylene, polyvinyl chloride, polyesters and composite materials. High strength polyamides may also be suitable. In additional to fusing, the various components may be joined by heat shrinking or use of an adhesives, such as acrylonitrile based adhesives.

The dimensions of catheter 10 are determined largely by the size of the guidewires to be employed and the size of the artery or other body lumen through which the catheter must pass. Generally, the diameter of the guidewire lumen 16 is sufficient to accommodate a guidewire 44 and to allow it to be slidably disposed therein. The diameters of guidewires for coronary use can vary from about 0.006 to about 0.035 inch (0.2–0.89 mm) in diameter, and the inner diameter of the guidewire lumen 18 of the catheter 10 should be about 0.001 to about 0.005 inch (0.025–0.127 mm) larger than the diameter of the guidewire. In one embodiment, the proximal section 12 and coaxial section of the distal section 13 have an outer diameter of about 0.034 in and the fused overlapped dual lumen portion 41 has an outer diameter of about 0.042 in.

The catheter shaft 11 is sufficiently long to extend from outside the proximal end of a guiding catheter, which likewise extends out of the patient, to a stenosis to be treated within the patient's vascular system (or other desired location therein), e.g. from about 100 to about 150 cm when a Seldinger approach through the femoral artery is employed to introduce the catheter 10 into the patient's vasculature. The intermediate shaft section is typically about 1 to about 30 cm long, and preferably about 5 to about 10 cm long. Preferably, the proximal guidewire port 26 is at least about 3 cm and may be up to about 60 cm from the distal end of the catheter shaft, and more preferably about 20 to about 50 cm. The mandrel 22 is typically about 80 to about 140 cm, preferably about 110 to about 120 cm in length.

The catheter 10 of the invention can be inserted into the patient in a conventional rapid exchange fashion with the guidewire 44 preloaded within the guidewire lumen 16 and extending proximally through proximal guidewire port 20. Catheter 10 may be withdrawn and a replacement catheter mounted onto the proximal end of guidewire 44 by inserting the proximal end of the guidewire through a distal guidewire port 19 in the distal end of the replacement rapid exchange type catheter and advancing the catheter over the guidewire disposed within a guidewire lumen 16 of the replacement catheter until the guidewire exits proximal guidewire port 20. The proximal end of the guidewire is held while the replacement catheter is advanced within the patient in a conventional manner.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. An intraluminal balloon catheter, comprising:
   an elongated catheter shaft having a proximal end, a distal end, a distal guidewire port in the distal end, and a proximal guidewire port spaced closer to the distal end than to the proximal end;
   an inflation lumen extending within the elongated catheter shaft;
   an inflatable balloon disposed on a distal catheter shaft section, having an interior in fluid communication with the inflation lumen;
   a guidewire receiving lumen extending through a portion of the elongated catheter shaft between and in fluid communication with the distal guidewire port and the proximal guidewire port; and
   a support mandrel disposed within the inflation lumen, having a distal end that is unattached and which extends distal of the proximal guidewire port;
   wherein the guidewire lumen and the inflation lumen are substantially parallel at the proximal guidewire port and coaxial distal of the proximal guidewire port.

2. The catheter of claim 1, wherein the support mandrel has a secured proximal end.

3. The catheter of claim 1, wherein the distal end of the support mandrel extends to a section of the catheter shaft where the guidewire lumen and the inflation lumen are coaxial.

4. The catheter of claim 1, wherein the mandrel has at least a first tapered section having a proximal end located proximal to the proximal guidewire port.

5. The catheter of claim 4, wherein the first tapered section of the mandrel has a distal end located distal to the proximal guidewire port.

6. The catheter of claim 1, wherein the mandrel includes a second tapered section proximal to the first tapered section.

7. The catheter of claim 1, further comprising a sleeve disposed within the inflation lumen and configured to receive a distal section of the support mandrel.

8. The catheter of claim 7, wherein the distal end of the support mandrel extends distally beyond the sleeve.

9. The catheter of claim 1, further comprising a sleeve disposed within the inflation lumen and configured to receive a distal section of the support mandrel.

10. The catheter of claim 9, wherein the distal end of the support mandrel extends distally beyond the distal end of the sleeve to a section of the catheter shaft where the guidewire lumen and the inflation lumen are coaxial.

11. The catheter of claim 10, wherein the sleeve distal end is within a section of the catheter shaft where the guidewire lumen and the inflation lumen are parallel.

12. The catheter of claim 9, wherein the sleeve is about 0.1 cm to about 150 cm long.

13. The catheter of claim 9, wherein a portion of the mandrel located proximal to the mandrel distal end is secured to the sleeve.

14. The catheter of claim 13, wherein the sleeve is secured to a wall of the catheter shaft defining the inflation lumen.

15. The catheter of claim 1, wherein the proximal guidewire port is proximal to the inflatable balloon.

* * * * *